US007687613B2

(12) United States Patent
Crystal et al.

(10) Patent No.: US 7,687,613 B2
(45) Date of Patent: Mar. 30, 2010

(54) GENETIC VACCINES DIRECTED AGAINST BACTERIAL EXOTOXINS

(75) Inventors: Ronald G. Crystal, New York, NY (US); Neil R. Hackett, New York, NY (US); Yadi Tan, Zhi-Jiang (CN)

(73) Assignee: Cornell Research Foundation, Inc., Ithaca, NY (US)

( * ) Notice: Subject to any disclaimer, the term of this patent is extended or adjusted under 35 U.S.C. 154(b) by 1167 days.

(21) Appl. No.: 10/649,457

(22) Filed: Aug. 27, 2003

(65) Prior Publication Data

US 2006/0019380 A1  Jan. 26, 2006

(51) Int. Cl.
*C12N 15/11* (2006.01)
*A61K 48/00* (2006.01)

(52) U.S. Cl. ........................................ 536/23.1; 514/44

(58) Field of Classification Search ................. 536/23.1; 514/44
See application file for complete search history.

(56) References Cited

U.S. PATENT DOCUMENTS

| | | | |
|---|---|---|---|
| 6,083,716 | A | 7/2000 | Wilson et al. |
| 6,348,450 | B1 | 2/2002 | Tang et al. |
| 6,500,641 | B1 | 12/2002 | Chen et al. |

OTHER PUBLICATIONS

Tan, Y et al. Human Gene Therapy 14(17):1673-1682, Nov. 23, 2003.*
Hamdan, FF et al. Paraitol Res 88:583-586, 2002.*
van Drunen Littel-van den Hurk, A et al. Immunol Rev 199:113-125, 2004.*
Bell et al., *Emerg. Infect. Dis.*, 8 (2), 222-225 (Feb. 2002).
Cieslak et al., *Emerg. Infect. Dis.*, 5 (4), 552-555 (Jul.-Aug. 1999).
Farina et al., *J. Virol.*, 75 (23), 11603-11613 (Dec. 2001).
Gu et al., *Vaccine*, 17, 340-344 (1999).
Iacono-Connors et al., *Infect. Immun.*, 59 (6). 1961-1965 (Jun. 1991).
Ingelsby et al., *JAMA*, 287, 2236-2252 (2002).
Ivins et al., *Eur. J. Epidemiol.*, 4, 12-19 (1988).
Ivins et al., *Vaccine*, 11-12, 1141-1148 (Jul. 1998).
Koide et al., *Japan J. Pharrnacol.*, 83, 167-174 (2000).
Lacy et al., *J. Biol. Chem.*, 277 (4), 3006-3010 (Jan. 25, 2002).
Little et al., *Infect. Immun.*, 52 (2), 509-512 (May 1986).
Malin et al., *Microbes Infect.*, 2 (14), 1677-1685 (Nov. 2, 2000).
Mogridge et al., *J. Bacteriol.*, 183 (6), 2111-2116 (Mar. 2001).
Narum et al., *Infect. Immun.*, 69 (12), 7250-7253 (Dec. 2001).
Pitt et al.,*J. Appl. Microbiol.*, 87, 304 (1999).
Price et al., *Infect. Immun.*, 69 (7), 4509-4515 (Jul. 2001).
Puziss et al., *Appl. Microbiol.*, 11, 330-334 (1963).
Puziss et al., *J. Bacteriol.*, 85, 230-236 (1962).
Sellman et al., *J. Biol. Chem.*, 276 (11), 8371-8376 (Mar. 16, 2001).
Sellman et al., *Science*, 292, 695-697 (Apr. 27, 2001).
Uchijima et al., *J. Immunol.*, 161, 5594-5599 (1998).
Welkos et al., *Microbiology*, 147, 1677-1685 (2001).
Wu et al., *Proc. Natl. Acad. Sci. USA*, 92, 11671-11674 (Dec. 1995).

* cited by examiner

*Primary Examiner*—Thaian N Ton
*Assistant Examiner*—Marcia S Noble
(74) *Attorney, Agent, or Firm*—Leydig, Voit & Mayer, Ltd.

(57) ABSTRACT

The invention provides a gene transfer vector comprising a humanized nucleic acid sequence encoding an immunogenic portion of one or more exotoxins of *Bacillus anthracis* and a heterologous sorting signal. The invention also provides a method of producing an immune response against *Bacillus anthracis* in a host comprising administering to the host the gene transfer vector.

13 Claims, No Drawings

GENETIC VACCINES DIRECTED AGAINST BACTERIAL EXOTOXINS

STATEMENT REGARDING FEDERALLY SPONSORED RESEARCH AND DEVELOPMENT

This invention was made in part with Government support under Grant Number U01HL66952-01 awarded by the National Heart, Lung, and Blood Institute (NHLBI). The Government may have certain rights in this invention.

FIELD OF THE INVENTION

This invention pertains to vaccines directed against exotoxins of pathogenic bacteria.

BACKGROUND OF THE INVENTION

In the last 50 years, only 236 people have been infected with anthrax in the United States. Although primarily a veterinary disease, the recent anthrax bioterrorism threat suggests that the incidence of anthrax in humans likely will increase. The disease is initiated by contact with anthrax spores and manifests as inhaled, cutaneous, and gastrointestinal forms, all of which can be fatal. Inhalation anthrax, however, has the highest mortality, with a survival rate of only 60% in the recent U.S. bioterrorism incidents (see, e.g., Inglesby et al., JAMA, 287, 2236-2252 (2002)).

The pathogenesis of many bacterial infections is dependent on extracellular proteins known as exotoxins. Exotoxins cause pathogenesis by a number of mechanisms, including tissue invasion, cell lysis, effects on neurotransmitter uptake and release, and disruption of cellular homeostasis. With respect to Bacillus anthracis, the causative agent of anthrax, pathogenesis is elicited by three exotoxins known as protective antigen (PA), edema factor (EF), and lethal factor (LF). PA is a proteolytically activated heptamer which binds to a specific cellular receptor and facilitates intracellular translocation of EF and/or LF. LF is a metalloprotease which acts on a variety of substrates including mitogen-activated protein kinase. EF induces fluid loss, possibly through elevation of intracellular cyclic AMP (camp) levels. Bacillus anthracis exotoxins are binary in that two Polypeptides are required for toxicity.

The anthrax vaccine that is currently available in the United States consists of a cell-free filtrate of a nonencapsulated attenuated strain of B. anthracis (Bioport Corporation, Lansing, Mich.), of which protective antigen is the major component (see, e.g., Puziss et al., J. Bacteriol., 85, 230-236 (1962), and Puziss et al., Appl. Microbiol., 11, 330-334 (1963)). The safety and efficacy of this vaccine in humans, however, remains the focus of intense investigation (see, e.g., Inglesby et al., supra). Indeed, several drawbacks associated with the vaccine have been reported, including the need for frequent boosters, the apparent inability to protect adequately against certain strains of B. anthracis, and occasional local immunogenicity (see, e.g., Ivins et al., Eur. J. Epidemiol., 4, 12-19 (1988)). In addition, an experimental vaccine based on recombinant PA with an Alhydrogel adjuvant is currently being developed by the U.S. Army, but has not yet been tested in humans (see, e.g., Ivins et al., Vaccine, 16, 1141-1148 (1998)).

Accordingly, there remains a need for alternative compositions and methods for protection against anthrax infection that elicit a rapid and efficient immune response in a broad spectrum of the population. The invention provides such a composition and method. These and other advantages of the invention, as well as additional inventive features, will be apparent from the description of the invention provided herein.

BRIEF SUMMARY OF THE INVENTION

The invention provides a gene transfer vector comprising a nucleic acid sequence which encodes at least an immunogenic portion of one or more exotoxins of Bacillus anthracis and a heterologous sorting signal, wherein the nucleic acid sequence comprises codons expressed more frequently in humans than in Bacillus anthracis. The invention also provides a method of producing an immune response against Bacillus anthracis in a host, which method comprises administering to the host the above-described gene transfer vector, wherein the nucleic acid sequence is expressed to produce the immunogenic portion of the one or more exotoxins in the host, thereby producing an immune response against Bacillus anthracis.

DETAILED DESCRIPTION OF THE INVENTION

The invention provides a gene transfer vector comprising a nucleic acid sequence which encodes at least an immunogenic portion of one or more exotoxins of Bacillus anthracis and a heterologous sorting signal. The nucleic acid sequence comprises codons expressed more frequently in humans than in Bacillus anthracis. The invention also provides a method of producing an immune response against Bacillus anthracis in a host, which method comprises administering to the host the above-described gene transfer vector, wherein the nucleic acid sequence is expressed to produce the immunogenic portion of the one or more exotoxins in the host, thereby producing an immune response against Bacillus anthracis. The use of a gene transfer vector, particularly a replication-deficient adenoviral vector, which encodes, using human-preferred codons, an immunogenic portion of one or more B. anthracis exotoxins, especially in combination with a heterologous sorting signal, offers an improvement over previously described B. anthracis vaccines by optimizing the humoral immune response directed against the pathogen and minimizing the number of booster administrations required. Various aspects of the inventive gene transfer vector and method are discussed below. Although each parameter is discussed separately, the inventive gene transfer vector and method comprise combinations of the parameters set forth below to evoke protection against anthrax infection in a human. Accordingly, any combination of parameters can be used according to the inventive gene transfer vector and the inventive method.

Gene Transfer Vector

A "gene transfer vector" is any molecule or composition that has the ability to carry a heterologous nucleic acid sequence into a suitable host cell where synthesis of the encoded protein takes place. Typically and preferably, a gene transfer vector is a nucleic acid molecule that has been engineered, using recombinant DNA techniques that are known in the art, to incorporate the heterologous nucleic acid sequence. Desirably, the gene transfer vector is comprised of DNA. Examples of suitable DNA-based gene transfer vectors include plasmids and viral vectors. However, gene transfer vectors that are not based on nucleic acids, such as liposomes, are also known and used in the art. The inventive gene transfer vector can be based on a single type of nucleic acid (e.g., a plasmid) or non-nucleic acid molecule (e.g., a lipid or a polymer). Alternatively, the gene transfer vector can be a combination of a nucleic acid molecule and a non-nucleic acid molecule (i.e., "chimeric"). For example, a plasmid harboring the heterologous nucleic acid sequence can be formulated with a lipid or a polymer as a delivery vehicle. Such a gene transfer vector is referred to herein as a "plasmid-lipid complex" or a "plasmid-polymer" complex, respectively. The inventive gene transfer vector can be integrated into the host cell genome, or can be present in the host cell in the form of an episome.

Preferably, the gene transfer vector is a viral vector. Suitable viral vectors include, for example, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. These viral vectors can be prepared using standard recombinant DNA techniques described in, for example, Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

An HSV-based viral vector is suitable for use as a gene transfer vector to introduce a nucleic acid into numerous cell types. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. Advantages of the HSV vector are its ability to enter a latent stage that can result in long-term DNA expression and its large viral DNA genome that can accommodate exogenous DNA inserts of up to 25 kb. Of course, the ability of HSV to promote long-term production of exogenous protein is potentially disadvantageous in terms of short-term treatment regimens. However, one of ordinary skill in the art has the requisite understanding to determine the appropriate vector for a particular situation. HSV-based vectors are described in, for example, U.S. Pat. Nos. 5,837,532, 5,846,782, 5,849,572, and 5,804,413, and International Patent Applications WO 91/02788, WO 96/04394, WO 98/15637, and WO 99/06583.

AAV vectors are viral vectors of particular interest for use in gene therapy protocols. AAV is a DNA virus, which is not known to cause human disease. The AAV genome is comprised of two genes, rep and cap, flanked by inverted terminal repeats (ITRs), which contain recognition signals for DNA replication and packaging of the virus. AAV requires co-infection with a helper virus (i.e., an adenovirus or a herpes simplex virus), or expression of helper genes, for efficient replication. AAV can be propagated in a wide array of host cells including human, simian, and rodent cells, depending on the helper virus employed. An AAV vector used for administration of a nucleic acid sequence typically has approximately 96% of the parental genome deleted, such that only the ITRs remain. This eliminates immunologic or toxic side effects due to expression of viral genes. If desired, the AAV rep protein can be co-administered with the AAV vector to enable integration of the AAV vector into the host cell genome. Host cells comprising an integrated AAV genome show no change in cell growth or morphology (see, e.g., U.S. Pat. No. 4,797,368). As such, prolonged expression of therapeutic factors from AAV vectors can be useful in treating persistent and chronic diseases.

The viral vector is most preferably an adenoviral vector. Adenovirus (Ad) is a 36 kb double-stranded DNA virus that efficiently transfers DNA in vivo to a variety of different target cell types. The adenoviral vector can be produced in high titers and can efficiently transfer DNA to replicating and non-replicating cells. The adenoviral vector genome can be generated using any species, strain, subtype, mixture of species, strains, or subtypes, or chimeric adenovirus as the source of vector DNA. Adenoviral stocks that can be employed as a source of adenovirus can be amplified from the human adenoviral serotypes 1 through 51, which are currently available from the American Type Culture Collection (ATCC, Manassas, Va.), or from any other serotype of human adenovirus available from any other source. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Given that the human adenovirus serotype 5 (Ad5) genome has been completely sequenced, the adenoviral vector of the invention is described herein with respect to the Ad5 serotype.

In addition to human adenovirus, the adenoviral vector can be generated using a non-human primate adenovirus, in which case, the adenovirus is preferably a chimpanzee adenovirus. Conceivably, the administration of a chimpanzee adenoviral vector to a human host may avoid the immune response often elicited by human adenoviral vectors as a result of pre-existing immunity to human adenovirus (see, e.g., U.S. Pat. No. 6,083,716). In this regard, the major neutralizing epitope of certain strains of chimpanzee adenovirus differ from those of corresponding human strains (see, e.g., Farina et al., *J. Virol.*, 75, 11603-11613 (2001)). Thus, humans have no pre-existing immunity against such strains of chimpanzee adenovirus. Adenoviral stocks that can be employed as a source of chimpanzee adenovirus can be amplified from the chimpanzee adenoviral strains C1 or CV68 ("C68"), which are currently available from the American Type Culture Collection (ATCC, Manassas, Va.), or from any other strain of chimpanzee adenovirus available from any other source. The C1 strain is most similar to human adenovirus of subgroup B, while the C68 strain is most similar to serotype 4 of human adenovirus (subgroup E). Accordingly, the gene regions of strain C1 have been identified by analyzing the sequence homology to the known gene regions of human Ad3, Ad5, and Ad7. Similarly, the gene regions of strain C68 have been identified through sequence comparisons with human Ad4 and Ad5 (see U.S. Pat. No. 6,083,716). Strain C68 has been shown to bind the same coxsackievirus and adenovirus receptor ("CAR") as human Ad5 for cell entry (see, e.g., Farina et al., supra).

Adenoviral vectors are well known in the art and are described in, for example, U.S. Pat. Nos. 5,559,099, 5,712,136, 5,731,190, 5,837,511, 5,846,782, 5,851,806, 5,962,311, 5,965,541, 5,981,225, 5,994,106, 6,020,191, 6,083,716, 6,113,913, and 6,482,616, U.S. Patent Application Publication Nos. 2001/0043922 A1, 2002/0004040 A1, 2002/0031831 A1, and 2002/0110545 A1, International Patent Applications WO 95/34671, WO 97/21826, and WO 00/00628, and Thomas Shenk, "Adenoviridae and their Replication," and M. S. Horwitz, "Adenoviruses," Chapters 67 and 68, respectively, in *Virology*, B. N. Fields et al., eds., 3d ed., Raven Press, Ltd., New York (1996).

Preferably, the adenoviral vector is replication-deficient. By "replication-deficient" is meant that the adenoviral vector comprises a genome that lacks at least one replication-essential gene function. A deficiency in a gene, gene function, gene, or genomic region, as used herein, is defined as a deletion of sufficient genetic material of the viral genome to impair or obliterate the function of the gene whose nucleic acid sequence was deleted in whole or in part. Replication-essential gene functions are those gene functions that are required for replication (i.e., propagation) of a replication-deficient adenoviral vector. Replication-essential gene functions are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA I and/or VA-RNA II). Preferably, the replication-deficient adenoviral vector comprises an adenoviral genome deficient in at least one replication-essential gene function of one or more regions of an adenoviral genome (e.g., two or more regions of an adenoviral genome so as to result in a multiply replication-deficient adenoviral vector). The one or more regions of the adenoviral genome are preferably selected from the group consisting of the E1, E2, and E4 regions. More preferably, the replication-deficient adenoviral vector comprises a deficiency in at least one replication-essential gene function of the E1 region (denoted an E1-deficient adenoviral vector), particularly a deficiency in a replication-essential gene function of each of the adenoviral E1A region and the adenoviral E1B region. In addition to such a deficiency in the E1 region, the recombinant adenovirus also can have a mutation in the major late promoter (MLP), as discussed in International Patent Application WO 00/00628. More preferably, the vector is deficient in at least one replication-essential gene function of the E1 region and at least part of the nonessential E3 region (e.g., an Xba I deletion of the E3 region) (denoted an E1/E3-deficient adenoviral vector). As with human adenovirus, chimpanzee adenovirus strain C68 can be rendered replication-deficient by deletion of the E1A and E1B gene regions.

Preferably, the adenoviral vector is "multiply deficient," meaning that the adenoviral vector is deficient in one or more gene functions required for viral replication in each of two or more regions of the adenoviral genome. For example, the aforementioned E1-deficient or E1/E3-deficient adenoviral vector can be further deficient in at least one replication-essential gene function of the E4 region (denoted an E1/E4-deficient adenoviral vector). An adenoviral vector deleted of the entire E4 region can elicit a lower host immune response.

Alternatively, the adenoviral vector lacks replication-essential gene functions in all or part of the E1 region and all or part of the E2 region (denoted an E1/E2-deficient adenoviral vector). Adenoviral vectors lacking replication-essential gene functions in all or part of the E1 region, all or part of the E2 region, and all or part of the E3 region also are contemplated herein. If the adenoviral vector of the invention is deficient in a replication-essential gene function of the E2A region, the vector preferably does not comprise a complete deletion of the E2A region, which is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196, 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that the multiply replication-deficient adenoviral vector contain this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral genome of serotype Ad5.

The adenoviral vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case it is preferred that at least either the viral inverted terminal repeats (ITRs) and one or more promoters or the viral ITRs and a packaging signal are left intact (i.e., an adenoviral amplicon). The larger the region of the adenoviral genome that is removed, the larger the piece of exogenous nucleic acid sequence that can be inserted into the genome. For example, given that the adenoviral genome is 36 kb, by leaving the viral ITRs and one or more promoters intact, the exogenous insert capacity of the adenovirus is approximately 35 kb. Alternatively, a multiply deficient adenoviral vector that contains only an ITR and a packaging signal effectively allows insertion of an exogenous nucleic acid sequence of approximately 37-38 kb. Of course, the inclusion of a spacer element in any or all of the deficient adenoviral regions will decrease the capacity of the adenoviral vector for large inserts. Suitable replication-deficient adenoviral vectors, including multiply deficient adenoviral vectors, are disclosed in U.S. Pat. Nos. 5,851,806 5,994,106, and 6,482,616, and International Patent Applications WO 95/34671 and WO 97/21826.

It should be appreciated that the deletion of different regions of the adenoviral vector can alter the immune response of the mammal. In particular, the deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509.

The adenoviral vector, when multiply replication-deficient, especially in replication-essential gene functions of the E1 and E4 regions, preferably includes a spacer element to provide viral growth in a complementing cell line similar to that achieved by singly replication-deficient adenoviral vectors, particularly an adenoviral vector comprising a deficiency in the E1 region. The spacer element can contain any sequence or sequences which are of the desired length. The spacer element sequence can be coding or non-coding and native or non-native with respect to the adenoviral genome, but does not restore the replication-essential function to the deficient region. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. The use of a spacer in an adenoviral vector is described in U.S. Pat. No. 5,851,806.

Alternatively, the adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. Replication of the adenoviral vector can be limited to a target tissue, thereby allowing greater distribution of the vector throughout the tissue while exploiting adenovirus' natural ability to lyse cells during the replication cycle, thereby providing a mechanism of destroying infected cells. Conditionally-replicating adenoviral vectors are described further in U.S. Pat. No. 5,998,205.

Construction of adenoviral vectors is well understood in the art. Adenoviral vectors can be constructed and/or purified using the methods set forth, for example, in U.S. Pat. Nos. 5,965,358, 5,994,128, 6,033,908, 6,168,941, 6,329,200, 6,383,795, 6,440,728, 6,447,995, and 6,475,757, and International Patent Applications WO 98/53087, WO 98/56937, WO 99/15686, WO 99/54441, WO 00/12765, WO 01/77304, and WO 02/29388, as well as other references identified herein. Moreover, numerous adenoviral vectors are available commercially. The production of adenoviral gene transfer vectors involves using standard molecular biological techniques such as those described in, for example, Sambrook et al., supra, Watson et al., supra, Ausubel et al., supra, and several of the other references mentioned herein.

Replication-deficient adenoviral vectors are typically produced in complementing cell lines that provide gene functions not present in the replication-deficient adenoviral vectors, but required for viral propagation, at appropriate levels in order to generate high titers of viral vector stock. A preferred cell line complements for at least one, and preferably all, replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons, which comprise minimal adenoviral sequences, such as only inverted terminal repeats (ITRs) and the packaging signal or only ITRs and an adenoviral promoter). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome.

The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication-competent adenoviruses (RCA) is minimized if not avoided in the vector stock, which, therefore, is suitable for certain therapeutic purposes, especially gene therapy purposes. The lack of RCA in the vector stock avoids the replication of the adenoviral vector in non-complementing cells.

The construction of complementing cell lines involves standard molecular biology and cell culture techniques, such as those described by Sambrook et al., supra, and Ausubel et al., supra. Complementing cell lines for producing the gene transfer vector (e.g., human or chimpanzee adenoviral vector) include, but are not limited to, 293 cells (described in, e.g., Graham et al., *J. Gen. Virol.*, 36, 59-72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., *J. Virol.*, 71, 9206-9213 (1997)).

Nucleic Acid Sequence Encoding *B. anthracis* Exotoxin

The inventive gene transfer vector comprises a nucleic acid sequence which encodes at least an immunogenic portion of one or more exotoxins of *Bacillus anthracis* (i.e., one or more nucleic acid sequences encoding one or more immunogenic portions of one or more exotoxins) and a heterologous sorting signal. The gene transfer vector comprises at least one nucleic acid sequence as described herein, i.e., the gene transfer vector can comprise one nucleic acid sequence as described herein or more than one nucleic acid sequence as described herein (i.e., two or more nucleic acid sequences). The nucleic acid sequence encoding the immunogenic portion can be obtained from any source, e.g., isolated from nature, synthetically generated, isolated from a genetically engineered organism, and the like. An ordinarily skilled artisan will appreciate that any type of nucleic acid sequence (e.g., DNA, RNA, and cDNA) that can be inserted into a gene transfer vector can be used in connection with the invention. The nucleic acid sequence can be recombinantly produced, or can be a genomic nucleic acid sequence. Typically and preferably, the nucleic acid sequence is transcribed and translated into a peptide, polypeptide, or protein. In some cases, however, the nucleic acid sequence is not translated, such as when the nucleic acid sequence encodes an antisense molecule or a ribozyme.

When the gene transfer vector is a replication-deficient adenovirus, the nucleic acid sequence encoding the protein is preferably located in the E1 region of the adenoviral genome. The insertion of a nucleic acid sequence into the adenoviral genome (e.g., the E1 region of the adenoviral genome) can be facilitated by known methods, for example, by the introduction of a unique restriction site at a given position of the adenoviral genome.

Whatever type of nucleic acid sequence is used, the nucleic acid sequence preferably encodes an immunogenic portion of one or more exotoxins of Bacillus anthracis. By "immunogenic portion" is meant any peptide, polypeptide, or portion thereof, that elicits an immune response (e.g., humoral and/or cell-mediated) against the organism from which it is obtained, derived, or based upon when introduced into a host. A sequence is "obtained" from a source when it is isolated from that source. A sequence is "derived" from a source when it is isolated from a source but modified in any suitable manner (e.g., by deletion, substitution, insertion, or other modification to the sequence) so as not to disrupt the normal function of the source gene. A sequence is "based upon" a source when the sequence is a sequence more than about 70% homologous (preferably more than about 80% homologous, more preferably more than about 90% homologous, and most preferably more than about 95% homologous) to the source but obtained through synthetic procedures (e.g., polynucleotide synthesis, directed evolution, etc.). Determining the degree of homology can be accomplished using any suitable method (e.g., BLASTnr, provided by GenBank).

Assessing the immunogenicity of an exotoxin, or portion thereof, can be determined using routine immunology techniques that are known in the art. With respect to humoral (i.e., antibody, immunoglobulin, or B cell) immune responses, for example, a suitable laboratory animal (e.g., a rabbit or mouse) can be immunized with a nucleic acid sequence encoding a candidate immunogenic portion of a B. anthracis exotoxin. Serum levels of antibodies specific for the polypeptide, protein, or protein portion encoded by the nucleic acid sequence can be detected and measured using any suitable method, including radioimmunoassay (RIA) and enzyme-linked immunosorbent assay (ELISA) (see, e.g., Abbas et al., eds., Cellular and Molecular Immunology, 4$^{th}$ ed., W. B. Saunders Company, Philadelphia (2000)). The cell-mediated (i.e., T cell) immune response elicited by expression of a nucleic acid sequence encoding a candidate immunogenic B. anthracis exotoxin can be assessed using, for example, the enzyme-linked immunospot (ELISPOT) assay. The ELISPOT assay enables detection of cells stimulated (e.g., by antigen) to produce cytokines. Preferably, the source cells for ELISPOT are isolated from the spleen and/or lymph nodes of immunized animals. The absence of a humoral or cell-mediated response to the polypeptide, protein, or protein portion encoded by the nucleic acid sequence indicates that the nucleic acid sequence does not encode an immunogenic portion of a B. anthracis exotoxin. These methods, however, are merely exemplary. Indeed, any method for determining the immunogenicity of a candidate exotoxin or portion thereof is within the scope of the invention.

In a preferred embodiment of the invention, the nucleic acid sequence encodes at least an immunogenic portion of one or more exotoxins of Bacillus anthracis. The one or more exotoxins preferably are selected from protective antigen (PA), lethal factor (LF), and edema factor (EF), taken individually or in any combination. As is common with other exotoxins that act intracellularly, the B. anthracis exotoxins are binary in that at least two different exotoxins are required to induce pathogenicity. In this respect, the nucleic acid sequence can encode at least an immunogenic portion of one exotoxin of B. anthracis, or, alternatively, an immunogenic portion of each of two or more exotoxins of B. anthracis. Preferably, the nucleic acid sequence encodes at least an immunogenic portion of protective antigen; however, nucleic acid sequences encoding immunogenic portions of lethal factor and/or edema factor are also within the scope of the invention.

Protective antigen is a 735 amino acid protein organized into four domains, and binds to an unidentified receptor on the surface of mammalian cells. When bound to its receptor, PA is cleaved by furin or a furin-like protease, which releases an amino-terminal PA fragment ($PA_{20}$) and leads to heptamerization of the remainder of the protein ($PA_{63}$) on the cell surface. $PA_{63}$ forms a complex with EF and LF, which is internalized by the cell via endocytosis. Acidification of the endosome induces a conformational change in the $PA_{63}$ heptamer, converting $PA_{63}$ into a membrane-spanning pore. EF and LF are then translocated through the pore into the cytosolic environment. PA appears to have no further role in the intoxication process (see, e.g., Mogridge et al., J. Bact., 183, 2111-2116 (2001), and Sellman et al., J. Biol. Chem., 276, 8371-8376 (2001)).

In one embodiment of the invention, the nucleic acid sequence preferably encodes a wild-type immunogenic portion of a B. anthracis exotoxin. Alternatively, however, when expression of a wild-type B. anthracis exotoxin is pathogenic in a host, such as when an immunogenic portion of two B. anthracis exotoxins (e.g., PA and LF, or PA and EF) is expressed in a host, the nucleic acid encodes a mutant form of the exotoxin that is immunogenic, but not pathogenic, in a host. A mutant exotoxin is preferably produced by introducing one or more mutations (e.g., point mutations, deletions, insertions, etc.) into the nucleic acid sequence encoding a naturally occurring exotoxin. Such mutations are introduced in the nucleic acid sequence to effect one or more amino acid substitutions in an encoded exotoxin. Thus, where mutations are introduced in the nucleic acid sequence encoding the exotoxin, such mutations desirably will effect a substitution in the encoded exotoxin whereby codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. In addition, the nucleic acid sequence can encode a homolog of an immunogenic portion of a wild-type or mutant B. anthracis exotoxin. A homolog of an immunogenic portion of a B. anthracis exotoxin, whether wild-type or mutant, can be any peptide, polypeptide, or portion thereof, that is more than about 70% identical (preferably more than about 80% identical, more preferably more than about 90% identical, and most preferably more than about 95% identical) to the immunogenic portion of the exotoxin at the amino acid level. The degree of amino acid identity can be determined using any method known in the art, such as the BLAST sequence database. Furthermore, a homolog of the exotoxin can be any peptide, polypeptide, or portion thereof, which hybridizes to the exotoxin under at least moderate, preferably high, stringency conditions. Exemplary moderate stringency conditions include overnight incubation at 37° C. in a solution comprising 20% formamide, 5× SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1× SSC at about 37-50° C., or substantially similar conditions, e.g., the moderately stringent conditions described in Sambrook et al., supra. High stringency conditions are conditions that use, for example (1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride and 75 mM sodium citrate at 42° C., or (3) employ 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at (i) 42° C. in 0.2× SSC, (ii) 55° C. in 50% formamide, and (iii) 55° C. in 0.1× SSC (preferably in combination with EDTA). Additional details and an explanation of stringency of hybridization reactions are provided in, e.g., Ausubel et al., supra.

When the nucleic acid sequence encodes a mutant form of, for example, protective antigen, the nucleic acid sequence can encode an oligomerization mutant of PA. It is believed that certain mutations in domain three of PA are required for heptamerization of PA. For example, a single mutation of PA amino acid 512 has been shown to be sufficient to prevent oligomerization (see, e.g., Mogridge et al., supra). However, any mutation that inhibits oligomerization of PA while preserving immunogenicity is within the scope of the invention. PA oligomerization mutants are described in, for example, Mogridge et al., supra. In addition or alternatively, the nucleic acid sequence can encode a PA mutant that is unable to translocate EF and LF across the endosome membrane into the cytosol. Such Pa. translocation mutants preferably have amino acid substitutions at residues 397, 425, and/or 427 of the PA polypeptide. PA translocation mutants are described in, for example, Sellman et al., supra, and Sellman et al., Science, 292, 695-697 (2001).

It is believed that the immune response to one antigen encoded by a pathogenic organism (e.g., a bacterium or virus) can be enhanced by co-expression of another unrelated antigen (see, e.g., Price et al., Infect. Immun., 69, 4509-4515 (2001)). Thus, in one embodiment of the invention, the nucleic acid sequence can encode an immunogenic portion of each of two or more exotoxins of B. anthracis. Preferably, the nucleic acid sequence encodes an immunogenic portion of PA and an immunogenic portion of LF or EF. As discussed above, PA, LF, and EF are non-toxic individually, but when expressed in binary or tertiary combinations, they produce toxic shock-like symptoms and, in many cases, death. In this embodiment, the nucleic acid sequence preferably encodes a mutant immunogenic portion of the B. anthracis PA exotoxin. In this respect, the immunogenic portion of PA can be derived from a nucleic acid sequence encoding any mutant or variant PA that retains immunogenicity, but not pathogenicity, in a host, such as those mutants or variants described herein. The immunogenic portion of LF or EF can be the wild-type, full length LF or EF protein, the PA-binding domain of LF or EF (i.e., amino acids 10-254) (see, e.g., Lacy et al., J. Biol. Chem., 277, 3006-3010 (2002)), or any other immunogenic portion of the LF or EF proteins. The nucleic acid can encode the immunogenic portion of each of two or more B. anthracis exotoxins in any combination. That is, the nucleic acid sequence can encode a mutant form of PA together with a wild-type or truncated form of LF and/or EF.

The expression of the nucleic acid sequence in the inventive gene transfer vector is controlled by a suitable expression control sequence operably linked to the nucleic acid sequence. An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. The nucleic acid sequence can be regulated by its endogenous promoter or by a normative promoter sequence. Examples of suitable normative promoters include the cytomegalovirus (CMV) immediate early (IE) promoter, the phosphoglycerate kinase (PGK) promoter, the long terminal repeat promoter of the Rous sarcoma virus (LTR-RSV), the sheep metallothionien promoter, and the human ubiquitin C promoter. Alternatively, expression of the nucleic acid sequence can be controlled by a chimeric promoter sequence. The promoter sequence is "chimeric" when it comprises at least two nucleic acid sequence portions obtained from, derived from, or based upon at least two different sources (e.g., two different regions of an organism's genome, two different organisms, or an organism combined with a synthetic sequence). The expression of the nucleic acid sequence in the inventive gene transfer vector is preferably regulated by the CMV IE promoter. Other preferred expression control sequences include the chicken β-actin promoter, the LTR-RSV promoter, the dendritic cell-specific dectin 2 promoter, and a chimeric expression control sequence comprising the CMV IE enhancer region and the chicken β-actin promoter. Suitable expression control sequences can be determined using eukaryotic expression systems such as are generally described in Sambrook et al., supra, and by using reporter gene systems (see, e.g., Taira et al., Gene, 263, 285-292 (2001)).

Preferably, the nucleic acid sequence in the inventive gene transfer vector further comprises a transcription-terminating region such as a polyadenylation sequence located 3' of the nucleic acid sequence. Any suitable polyadenylation sequence can be used, including a synthetic polyadenylation sequence, as well as the polyadenylation sequence of BGH (Bovine Growth Hormone), polyoma virus, SV40 (Human Sarcoma Virus-40), TK (Thymidine Kinase), EBV (Epstein Barr Virus), and the papillomaviruses, including human papillomaviruses and BPV (Bovine Papilloma Virus).

Heterologous Sorting Signal

The nucleic acid sequence contained in the inventive gene transfer vector encodes a heterologous sorting signal. The term "sorting signal," as used herein, refers to an amino acid sequence found in a protein that selectively guides the distribution of the protein to specific subcellular compartments. For example, sorting signals can direct proteins to intracellular organelles for uptake and processing. The nucleic acid sequence in the inventive gene transfer can further comprise a heterologous signal peptide. The term "signal peptide," as used herein, refers to a peptide, typically located at the amino terminus of a protein, which targets the protein to specific cellular compartments, such as the endoplasmic reticulum, and directs secretion of the mature protein from the cell in which it is produced. Unlike sorting signals, which can comprise a portion of the mature protein in which they are found, signal peptides typically are removed from a precursor polypeptide and, thus, are not present in mature proteins. The sorting signal and signal peptide are "heterologous" in that either is not obtained from, derived from, or based upon a naturally occurring sorting signal or signal peptide of B. anthracis. By "naturally occurring" is meant that the sorting signal or signal peptide is encoded by a nucleic acid sequence that can be found in nature and has not been synthetically modified. Notwithstanding the foregoing, however, the nucleic acid sequence that encodes a heterologous sorting signal or signal peptide can be naturally found in B. anthracis, but located at a normative position with respect to the immunogenic portion of one or more exotoxins of *B. anthracis* and/or operably linked to a normative promoter.

Preferably, the heterologous sorting signal directs the exotoxin to a subcellular sorting pathway. The subcellular sorting pathway is selected from the group consisting of an extracellular pathway, a cytoplasmic pathway, a cell membrane pathway, a lysosome pathway, an endoplasmic reticulum pathway, and a degradative pathway, although sorting signals which direct the exotoxin to other subcellular sorting pathways known in the art are within the scope of the invention.

The heterologous sorting signal desirably directs the immunogenic portion of the inventive *B. anthracis* exotoxin to a subcellular sorting pathway that is involved in antigen presentation. It is believed that protection against anthrax infection primarily depends upon humoral immune responses (see, e.g., Gu et al., *Vaccine*, 17, 340-344 (1999); Pitt et al., *J. Appl. Microbiol.*, 87, 304 (1999); Welkos et al., *Microbiology*, 147, 1677-1685 (2001)). The humoral immune response is mediated, in part, by the major histocompatability class II (MHC II) antigen presentation pathway. Antigens can be presented on MHC II peptides through an exogenous mechanism, involving antigen uptake by antigen presenting cells from the extracellular environment and subsequent degradation in acidic endosomal and lysosomal vesicles, leading to epitope presentation by MHC II peptides to CD4+ T cells ("helper T cells") at the cell surface. Alternatively, antigens produced within antigen presenting cells also can be presented via the MHC II pathway (see, e.g., U.S. Pat. No. 6,500,641). This mechanism for MHC II presentation, while not completely understood, has been demonstrated by targeting viral antigens to the lysosomal compartment by addition of a sorting signal isolated from various lysosomal-associated proteins.

Desirably, the heterologous sorting signal is any suitable heterologous sorting signal that directs the immunogenic portion of the one or more exotoxins of *Bacillus anthracis* to a lysosomal compartment in a host cell such that it is presented by MHC II peptides at the cell surface, thereby eliciting a humoral immune response against *B. anthracis*. Most preferably, the heterologous sorting signal is a lysosomal-associated membrane protein-1 (LAMP-1) sorting signal. LAMP-1 is a type 1 transmembrane protein that localizes predominantly to lysosomes and late endosomes (see, e.g., Wu et al., *Proc. Natl. Acad. Sci., USA*, 92, 11671-11675 (1995)). The LAMP-1 sorting signal comprises the transmembrane and cytoplasmic domains of the LAMP-1 protein. The nucleic acid sequence in the inventive gene transfer vector, therefore, preferably encodes the transmembrane and cytoplasmic domains of LAMP-1. Another suitable heterologous sorting signal includes, for example, the C-terminal tail of the lysosomal integral membrane protein II (LIMP-II). One of ordinary skill in the art will appreciate that the presence of a heterologous signal peptide in the polypeptide or protein encoded by the inventive nucleic acid sequence mediates translocation of the polypeptide or protein to the endoplasmic reticulum, from which the polypeptide or protein is directed to lysosomal or endosomal compartments via the heterologous sorting signal. Any signal peptide that directs secretion of the polypeptide or protein encoded by the nucleic acid sequence is suitable for use in the inventive gene transfer vector. The heterologous signal peptide is preferably a LAMP-1 signal peptide. The nucleic acid sequence in the inventive gene transfer vector desirably is constructed such that, when expressed, the heterologous signal peptide and the heterologous sorting signal are located at the N-terminus and C-terminus, respectively, of the polypeptide or protein encoded by the nucleic acid sequence. In addition to signal peptides, other mechanisms for secretion may be employed, such as, for example, truncation, deletion, or point mutation of secretion-inhibiting sequences present in the nucleic acid sequence.

Humananized *B. anthracis* Exotoxin Sequences

In accordance with the invention, the nucleic acid sequence which encodes at least an immunogenic portion of one or more exotoxins of *Bacillus anthracis* comprises codons expressed more frequently in humans than in *Bacillus anthracis*. While the genetic code is generally universal across species, the choice among synonymous codons is often species-dependent. Infrequent usage of a particular codon by an organism likely reflects a low level of the corresponding transfer RNA (tRNA) in the organism. Thus, introduction of a nucleic acid sequence into an organism which comprises codons that are not frequently utilized in the organism may result in limited expression of the nucleic acid sequence. One of ordinary skill in the art would appreciate that, to achieve maximum protection against *B. anthracis* infection, the inventive gene transfer vector must be capable of expressing high levels of *B. anthracis* exotoxins in a human host. In this respect, the inventive nucleic acid sequence encodes the native amino acid sequence of the immunogenic portion of the one or more *B. anthracis* exotoxins, but comprises codons that are expressed more frequently in humans than in *Bacillus anthracis*. Such modified nucleic acid sequences are commonly described in the art as "humanized" or as utilizing "human-preferred" codons.

In general, *B. anthracis* toxin genes are rich in adenosine (A) and thymine (T) nucleotides, resulting in a preference for codons that use an A or T at the third position, some of which are not commonly used in human genes. Thus, in the context of the invention, a *B. anthracis* nucleic acid sequence is said to be "humanized" if at least about 60% (e.g., at least about 70%, at least about 80%, or at least about 90%) of the wild-type codons in the nucleic acid sequence are modified to encode human-preferred codons. That is, a *B. anthracis* nucleic acid sequence is humanized if at least about 60% of the codons encoded therein are human-preferred codons. Preferred humanized nucleic acid sequences encoding PA, LF, and EF are set forth in SEQ ID NO:1, SEQ ID NO:2, and SEQ ID NO:3, respectively. However, the invention is not limited to these exemplary sequences. Indeed, genetic sequences can vary between different strains, and this natural scope of allelic variation is included within the scope of the invention. Additionally and alternatively, the humanized nucleic acid sequence encoding *B. anthracis* PA, LF, and/or EF exotoxins can be any sequence that hybridizes to SEQ ID NO:1, SEQ ID NO:2, or SEQ ID NO:3 under at least moderate, preferably high, stringency conditions, such as those described herein. Determining the degree of homology can be accomplished using any suitable method (e.g., BLASTnr, provided by GenBank).

Gene Transfer Vector Targeting

To enhance the immune response produced by the inventive gene transfer vector when administered to a host, the gene transfer vector desirably is modified such that it preferentially transduces antigen presenting cells. Antigen presenting cells (APCs) include, for example, dendritic cells (DC), macrophages, and monocytes. By transducing and transferring nucleic acid sequences into antigen presenting cells directly, particularly dendritic cells, antigen presentation is enhanced, conceivably resulting in lower required doses of the gene transfer vector as compared to an unmodified gene transfer vector; To direct the inventive gene transfer vector to the desired antigen presenting cells, its natural tropism for other types of cells preferably is attenuated or eliminated.

In one embodiment of the invention, the gene transfer vector is an adenoviral vector, preferably a replication-deficient adenoviral vector. The coat protein of the adenoviral vector can be manipulated to alter the binding specificity or recognition of the adenoviral vector for a viral receptor on a potential host cell. Such manipulations can include deletion of regions of the fiber, penton, hexon, pIIIa, pVI, and/or pIX, insertions of various native or non-native ligands into portions of the coat protein, and the like. Manipulation of the coat protein can broaden the range of cells infected by the adenoviral vector or enable targeting of the adenoviral vector to a specific cell type.

For example, in one embodiment, the adenoviral vector comprises a chimeric coat protein (e.g., a fiber, hexon, pIX, pIIIa, or penton protein), which differs from the wild-type (i.e., native) coat protein by the introduction of a normative amino acid sequence, preferably at or near the carboxyl terminus. Preferably, the normative amino acid sequence is inserted into or in place of an internal coat protein sequence. The normative amino acid sequence can be inserted within the internal coat protein sequence or at the end of the internal coat protein sequence. The resultant chimeric viral coat protein is able to direct entry into cells of the adenoviral vector comprising the coat protein that is more efficient than entry into cells of an adenoviral vector that is identical except for comprising a wild-type viral coat protein rather than the chimeric viral coat protein. Preferably, the chimeric coat protein binds a novel endogenous binding site present on the cell surface that is not recognized, or is poorly recognized, by an adenoviral vector comprising a wild-type coat protein. One direct result of this increased efficiency of entry is that the adenoviral vector can bind to and enter cell types which an adenovirus comprising wild-type coat protein typically cannot enter or can enter with only a low efficiency. If desired, native binding of the adenoviral coat proteins, e.g., the fiber or penton base, can be ablated.

Adenovirus infection of dendritic cells (DC) is mediated primarily through the interaction of the Arg-Gly-Asp (RGD) domain of the penton base protein and integrin molecules expressed at high levels on the surface of DC. A serotype 5 adenovirus engineered to express an additional RGD domain in the fiber knob infects dendritic cells at least 50-fold more effectively than an adenovirus with a wild-type capsid. Thus, in one embodiment of the invention, the gene transfer vector is an adenoviral vector in which the fiber protein has been manipulated to contain an RGD domain, such that the adenoviral vector transduces antigen presenting cells, preferably dendritic cells, more efficiently than an adenoviral vector with a wild-type fiber protein.

In another embodiment, the inventive gene transfer vector is an adenoviral vector in which the native tropism of the adenoviral fiber and penton proteins has been ablated. Ablation of native binding of fiber and penton proteins is preferably achieved by deletion of the CAR binding domain and deletion of the RGD domain, respectively (i.e., F$^-$/PB$^-$). Adenovirus containing deletions of the fiber CAR domain and penton RGD domain recognize and infect antigen presenting cells in the liver more efficiently than an adenovirus comprising wild-type coat proteins. The above-described F$^-$/PB$^-$ adenoviral vectors can be further manipulated to broaden and enhance targeting to antigen presenting cells. In this embodiment, the fiber protein of an F$^-$/PB$^-$ adenoviral vector can be engineered to express a ligand that specifically binds, for example, dendritic cells. Such ligands preferably comprise peptide sequences that bind preferentially to dendritic cells versus other cell types, and include, for example, antibodies or fragments thereof that bind specific DC cell surface markers (e.g., CD40). DC-binding peptide sequences can be identified using any suitable technique known in the art, such as phage display libraries. Phage display libraries have been utilized to identify peptide ligands in vivo (see, for example, U.S. Pat. No. 5,622,699), and are further described in Nicklin et al., *Mol. Ther.*, 4, 534-542 (2001), and Work et al., *Methods Enzymol.*, 346, 157-176 (2002). Once putative DC-specific ligands are identified, preferential infection and gene transfer to DC can be established in vitro prior to assessment of DC tropism in vivo, using viral entry assays that employ adenoviruses engineered to express a reporter gene.

In another embodiment, the gene transfer vector is an adenoviral vector comprising a chimeric virus coat protein not selective for a specific type of eukaryotic cell. The chimeric coat protein differs from the wild-type coat protein by an insertion of a normative amino acid sequence into or in place of an internal coat protein sequence. For example, a ligand comprising about five to about nine lysine residues (preferably seven lysine residues) is attached to the C-terminus of the adenoviral fiber protein via a non-coding spacer sequence. In this embodiment, the chimeric virus coat protein efficiently binds to a broader range of eukaryotic cells than a wild-type virus coat, including dendritic cells, such as described in International Patent Application WO 97/20051.

The specificity of binding of an adenoviral vector to a given cell also can be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenoviral vector to a given cell. Alternatively, use of an adenovirus comprising a short-shafted fiber enables targeting of the adenovirus to a desired cell-surface receptor by the introduction of a normative amino acid sequence either into the penton base or the fiber knob.

Of course, the ability of an adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type.

Suitable modifications to an adenoviral vector are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, and 6,465,253, U.S. Patent Application Publication Nos. 2001/0047081 A1, 2002/0099024 A1, and 2002/0151027 A1, and International Patent Applications WO 96/07734, WO 96/26281, WO 97/20051, WO 98/07865, WO 98/07877, WO 98/40509, WO 98/54346, WO 00/15823, WO 01/58940, and WO 01/92549.

Pharmaceutical Composition

The pharmaceutical composition of the invention comprises a pharmaceutically acceptable carrier and the inventive gene transfer vector comprising the nucleic acid sequence encoding an immunogenic portion of one or more exotoxins of *Bacillus anthracis*. Any suitable pharmaceutically acceptable carrier can be used within the context of the invention, and such carriers are well known in the art. The choice of carrier will be determined, in part, by the particular site to which the pharmaceutical composition is to be administered and the particular method used to administer the pharmaceutical composition. The following formulations are merely exemplary and are in no way limiting. However, oral, injectable, and aerosol formulations are preferred.

Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for aerosol administration comprise the inventive gene transfer vector, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Other suitable formulations are possible, for example, suppositories can be prepared by use of a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

More preferably, the pharmaceutical composition is formulated to protect the gene transfer vector from damage prior to administration. For example, in embodiments where the gene transfer vector is an adenoviral vector, the particular formulation desirably decreases the light sensitivity and/or temperature sensitivity of the adenoviral vector. Indeed, the pharmaceutical composition will be maintained for various periods of time and, therefore, should be formulated to ensure stability and maximal activity at the time of administration. Typically, the pharmaceutical composition is maintained at a temperature above 0° C., preferably at 4° C. or higher (e.g., 4-10° C.). In some embodiments, it is desirable to maintain the pharmaceutical composition at a temperature of 10° C. or higher (e.g., 10-20° C.), 20° C. or higher (e.g., 20-25° C.), or even 30° C. or higher (e.g., 30-40° C.). The pharmaceutical composition can be maintained at the aforementioned temperature(s) for at least 1 day (e.g., 7 days (1 week) or more), though typically the time period will be longer, such as at least 3, 4, 5, or 6 weeks, or even longer, such as at least 10, 11, or 12 weeks, prior to administration to a patient. During that time period, the adenoviral gene transfer vector optimally loses no, or substantially no, activity, although some loss of activity is acceptable, especially with relatively higher storage temperatures and/or relatively longer storage times. Preferably, the activity of the adenoviral vector composition decreases about 20% or less, preferably about 10% or less, and more preferably about 5% or less, after any of the aforementioned time periods.

To this end, the pharmaceutical composition preferably comprises a pharmaceutically acceptable liquid carrier, such as, for example, those described above, and a stabilizing agent selected from the group consisting of polysorbate 80, L-arginine, polyvinylpyrrolidone, α-D-glucopyranosyl α-D-glucopyranoside dihydrate (commonly known as trehalose), and combinations thereof. More preferably, the stabilizing agent is trehalose, or trehalose in combination with polysorbate 80. The stabilizing agent can be present in any suitable concentration in the pharmaceutical composition. When the stabilizing agent is trehalose, the trehalose desirably is present in a concentration of about 2-10% (wt./vol.), preferably about 4-6% (wt./vol.) of the pharmaceutical composition. When trehalose and polysorbate 80 are present in the pharmaceutical composition, the trehalose preferably is present in a concentration of about 4-6% (wt./vol.), more preferably about 5% (wt./vol.), while the polysorbate 80 desirably is present in a concentration of about 0.001-0.01% (wt./vol.), more preferably about 0.0025% (wt./vol.). When a stabilizing agent, e.g., trehalose, is included in the pharmaceutical composition, the pharmaceutically acceptable liquid carrier preferably contains a saccharide other than trehalose. Suitable formulations of the pharmaceutical composition are further described in U.S. Pat. No. 6,225,289 and International Patent Application WO 00/34444.

When the inventive gene transfer vector is an adenoviral vector, the pharmaceutical composition can further be formulated to reduce adherence loss of the adenoviral vector on devices used to prepare, store, or administer the adenoviral vector, such as glassware, syringes, or needles. Use of such a pharmaceutical composition will extend the shelf life of the pharmaceutical composition, facilitate administration, and increase the efficacy of the inventive method. In this regard, the pharmaceutical composition also can be formulated to enhance the spread of the adenoviral vector throughout the target tissue and/or enhance transduction efficiency. To this end, the pharmaceutical composition also can comprise hyaluronidase, which has been shown to enhance uptake of adenoviral vectors. Addition of proteases to the pharmaceutical composition can enhance the spread of the adenoviral vector throughout the target tissue. The adenoviral vectors of the pharmaceutical composition can be bound to biocompatible solid carriers, such as particulate carriers (e.g., beads, wafers, etc.), that remain in the target tissue due to size, or incorporated into a matrix, such as gel or foam.

In addition, the pharmaceutical composition can comprise additional therapeutic or biologically-active agents. For example, therapeutic factors useful in the treatment of a particular indication can be present. Factors that control inflammation, such as ibuprofen or steroids, can be part of the pharmaceutical composition to reduce swelling and inflammation associated with in vivo administration of the gene transfer vector and physiological distress. Immune system suppressors can be administered with the pharmaceutical composition to reduce any immune response to the gene transfer vector itself or associated with a disorder. Alternatively, immune enhancers can be included in the pharmaceutical composition to upregulate the body's natural defenses against disease. Moreover, cytokines can be administered with the pharmaceutical composition to attract immune effector cells to the infection site.

Anti-angiogenic factors, such as soluble growth factor receptors, growth factor antagonists, i.e., angiotensin, and the like, also can be part of the pharmaceutical composition. Similarly, vitamins and minerals, anti-oxidants, and micronutrients can be co-administered with the pharmaceutical composition. Antibiotics, i.e., microbicides and fungicides, can be present to reduce the risk of infection associated with gene transfer procedures and other disorders.

Method of Producing an Immune Response

The invention further provides a method of producing an immune response against *Bacillus anthracis* in a host. The inventive method comprises administering to the host a gene transfer vector having a nucleic acid sequence which encodes at least an immunogenic portion of one or more exotoxins of *Bacillus anthracis* and a heterologous signal peptide, wherein the nucleic acid sequence comprises codons expressed more frequently in humans than in *Bacillus anthracis*, and wherein the nucleic acid sequence is expressed to produce the immunogenic portion of the one or more exotoxins in the host, thereby producing an immune response against *Bacillus anthracis*. The inventive method desirably produces maximum levels of humoral immunity against *B. anthracis* infection within a short time period, while minimizing or eliminating the need for repeat administrations to maintain immunity. Descriptions of the gene transfer vector, the nucleic acid sequence, the pharmaceutical composition, and components thereof set forth above in connection with the inventive gene transfer vector also are applicable to those same aspects of the aforesaid inventive method.

The inventive method is desirably performed in vivo, preferably within a mammal, and most preferably within a human. When the method is applied in vivo, the invention provides a method of administering (i.e., inoculating or immunizing) the inventive gene transfer to a host, most preferably a human host. In accordance with the method, the gene transfer vector, such as is set forth above, is introduced into the host under conditions sufficient for the host to mount an immune response against the immunogenic portion of the one or more exotoxins of *B. anthracis*. While many methods of administration are known in the art, oral administration, intramuscular injection, and subdermal (i.e., subcutaneous) injection are preferred.

Whatever method is chosen to administer the inventive gene transfer vector in accordance with the inventive method, preferably the gene transfer vector is administered to antigen presenting cells of the host. Most preferably, the gene transfer vector is administered to dendritic cells of the host. As described above in connection with the inventive gene transfer vector, the gene transfer vector can be manipulated to ablate the natural tropism of the gene transfer vector, and introduce a new tropism for antigen presenting cells. The methods for modifying gene transfer vectors, particularly the coat proteins of adenoviral vectors, to preferentially bind dendritic cells are described above, and are applicable to this embodiment of the inventive method.

The dose of the inventive gene transfer vector administered to a mammal, particularly a human, in the context of the invention will vary with the particular gene transfer vector, the composition containing the gene transfer vector, the method of administration, and the particular site being treated. The dose should be sufficient to effect a desirable response, preferably a humoral immune response against *B. anthracis* infection, within a desirable time frame. When the inventive gene transfer vector is an adenoviral vector, typical doses will contain at least about $1\times10^5$ particle units (pu) of the adenoviral vector (e.g., at least about $1\times10^6$ pu), preferably at least about $1\times10^7$ pu (e.g., at least about $1\times10^8$ pu). Higher doses also can be used, such as doses of at least about $1\times10^9$ pu (e.g., at least about $1\times10^{10}$ pu), or even at least about $1\times10^{11}$ pu (e.g., at least about $1\times10^{12}$ pu), or even higher, such as at least about $1\times10^{13}$ pu (e.g., at least about $1\times10^{14}$ pu). Generally, dosages will be about $1\times10^5$-$1\times10^{14}$ PU (e.g., about $1\times10^7$-$1\times10^{13}$ pu), preferably $1\times10^8$-$1\times10^{12}$ pu (e.g., about $1\times10^9$-$1\times10^{11}$ pu).

With respect to the number of administrations of the inventive gene transfer vector, the most preferred dosing schedule involves a single administration of a dose of the gene transfer vector to the host. However, if a single administration of the inventive gene transfer vector does not elicit a sufficient humoral immune response against *B. anthracis* infection, a second dose can be administered to the host. The inventive method preferably comprises no more than two administrations of the inventive gene transfer vector to any one host. Where the gene transfer vector is an adenoviral vector and a second administration of the adenoviral vector is required, the first and second administrations can employ any combination of adenovirus strains. For example, the first administration can employ a human adenovirus, while the second administration can employ a chimpanzee adenovirus, and vice versa. In that human adenovirus serotype 5 and chimpanzee adenovirus strain C68 are preferred for use in connection with the inventive method, possible combinations of first and second administrations include: (i) Ad5 followed by Ad5, (ii) Ad5 followed by AdC68, (iii) AdC68 followed by AdC68, and (iv) AdC68 followed by Ad5.

Other Considerations

In addition to utilizing heterologous signal peptides, the humoral immune response to anthrax infection also can be enhanced by potentiating the interaction of anthrax exotoxins expressed by the gene transfer vector with antigen presenting cells (e.g., dendritic cells). Thus, in particular embodiments of the invention, the nucleic acid sequence can encode a genetic adjuvant to enhance the participation of dendritic cells in the humoral immune response. A genetic adjuvant desirably enhances dendritic cell (DC) participation by either activating dendritic cells upon introduction or infection of the inventive gene transfer vector, or by recruiting more dendritic cells to the site of gene transfer vector introduction or infection. The nucleic acid sequence may encode any suitable genetic adjuvant known in the art that activates or recruits dendritic cells, such as, for example, a cytokine. When the nucleic acid sequence encodes a genetic adjuvant that activates dendritic cells, preferred genetic adjuvants include CD40 ligand (CD40L), p65RHD, which is the N-terminal fragment of the p65, cRel NF6B gene, and intercellular adhesion molecule (ICAM). When the nucleic acid sequence encodes a genetic adjuvant that recruits dendritic cells to the site of infection, preferred genetic adjuvants include MIP3-α, SDF1, and MDC. The nucleic acid sequence can encode one or more genetic adjuvants in any combination. In this respect, the nucleic acid sequence can encode (i) one or more DC-activating adjuvant(s), (ii) one or more DC-recruiting adjuvant(s), or (iii) one or more DC-activating adjuvant(s) and one or more DC-recruiting adjuvant(s).

The inventive method can be performed in combination with other methods for the prophylaxis or treatment of *B. anthracis* infection. In one embodiment, the inventive gene transfer vector can be administered in conjunction with an existing anthrax vaccine, such as the U.S. anthrax vaccine available from Bioport Corporation, and the rPA/Alhydrogel vaccine described elsewhere herein. In addition, the inventive gene transfer vector can be administered before, after, or concurrently with antibiotics approved for use in managing *B. anthracis* infection. Such antibiotics include ciproflaxin, doxycycline, and penicillin G. Alternatively, levofloxacin or ofloxzcin may be administered instead of ciproflaxin (see, e.g., Cieslak et al., *Emerg. Infect. Dis.*, 5, 552-555 (1999), and Bell et al., *Emerg. Infect. Dis.*, 8, 222-225 (2002)). In addition, other therapeutic methods suggested in the art to exhibit anti-exotoxin properties can be used in conjunction with the inventive method. Such therapies include the use of clindamycin, steroids (particularly for the treatment of cutaneous forms of anthrax), angiotensin-converting enzyme (ACE) inhibitors, calcium channel blockers and tumor necrosis factor inhibitors (see, e.g., Bell et al., *supra*).

Because *B. anthracis* is an infectious agent which causes serious, and sometimes lethal, disease as a result of inhalation, all manipulations involving any component of the *B. anthracis* pathogen (e.g., the *B. anthracis* genome, spores, proteins, etc.) must be performed in accordance with Biosafety Level 3 (BSL 3) regulations as set forth by the Centers For Disease Control and Prevention (CDC).

The following examples further illustrate the invention but, of course, should not be construed as in any way limiting its scope.

EXAMPLE 1

This example demonstrates the generation of a gene transfer vector comprising a nucleic acid sequence encoding an immunogenic portion of protective antigen of *Bacillus anthracis* and a heterologous sorting signal, wherein the nucleic acid sequence comprises codons expressed more frequently in humans than in *Bacillus anthracis*.

Using routine molecular biology techniques, plasmids were constructed to express a nucleic acid sequence encoding *B. anthracis* protective antigen comprising human-preferred codons (hPA), the sequence of which is set forth in SEQ ID NO:1. Plasmid sec-hPA contains a nucleic acid sequence encoding the cleavable LAMP-1 signal peptide and the nucleic acid sequence encoding hPA, which was designed to direct the secretion of hPA. Plasmid sec-hPA-LAMP1 is identical to the sec-hPA plasmid, but was further engineered to express the LAMP-1 sorting signal (described in, e.g., Wu et al., *supra*) at the C-terminus of hPA. The sec-hPA-LAMP1 plasmid was designed to target hPA to the endosome/lysosome compartment. Both constructs were cloned into expression plasmids and operably linked to the cytomegalovirus immediate-early (CMV IE) promoter-enhancer. In addition, the sec-hPA-LAMP-1 expression construct was inserted into the E1 region of a replication-deficient adenoviral vector of serotype 5 (AdsechPA), using techniques known in the art and described herein. An E1-deficient adenoviral vector without any transgene (AdNull) was used as a control. The resulting adenoviral vector was propagated in 293 cells (see Graham et al., *supra*), which complement for E1 deficiencies.

To test for expression of hPA and for induction of an anti-hPA immune response, the plasmids and adenoviral vectors were administered to C57B1/6 (B6) mice by intramuscular injection. Specifically, the mice received 50 µg plasmid/100 µl PBS, or $10^9$ particle units (pu) of adenoviral vector. At two weeks post injection, blood was drawn and assessed by ELISA for the presence of anti-PA antibodies. Recombinant hPA was recognized by serum from mice immunized by the sec-hPA-LAMP-1 plasmid but not by serum from mice injected with the sec-hPA plasmid. In addition, the AdsechPA vector produced a higher anti-PA antibody titer in immunized mice than did the sec-hPA-LAMP1 plasmid vector.

The results of this example demonstrate the production of a gene transfer vector comprising a nucleic acid encoding a humanized immunogenic portion of *Bacillus anthracis* protective antigen and a heterologous sorting signal.

EXAMPLE 2

This example demonstrates a method of producing an immune response against *Bacillus anthracis* in a host by administering the inventive gene transfer vector to the host.

The immune response to a single intramuscular administration of AdsechPA (see Example 1) in BALB/c mice was compared with the recombinant PA protein/Alhydrogel vaccine (rPA/Alhydrogel) described herein, which was generated as described in Little and Knudson, *Infect. Immun.*, 52, 509-512 (1986). In this respect, a dose of $3\times10^9$ pu of AdsechPA and a 25 µg dose of the rPA/Alhydrogel vaccine were administered separately to BALB/c mice. Saline injections and Adnull were administered as controls. Anti-PA antibody production was assessed using ELISA.

A time course study of anti-PA IgG titer demonstrated that, at two weeks post administration, the IgG levels produced by each vaccine diverged, with the AdsechPA vaccine yielding a 10-fold higher titer. Assessment of IgG subclasses showed that, at four weeks post administration, the AdsechPA and rPA/Alhydrogel vaccines induced similar titers of IgG1, but the AdsechPA vaccine yielded greater than 200-fold higher IgG2a, IgG2b, and IgG3 titers than the rPA/Alhydrogel vaccine. The time course study also demonstrated that, over time, the 109 dose of AdsechPA yielded higher anti-lethal toxin (i.e., PA+LF) neutralizing antibody titers than the rPA/Alhydrogel vaccine. Indeed, at two weeks post administration, the AdsechPA vaccine elicited a neutralizing antibody titer of greater than $10^2$, while the neutralizing antibody titer elicited by the rPA/Alhydorgel vaccine was barely detectable In addition, immunized mice were challenged with lethal toxin by intravenous injection of mixed rPA and recombinant LF. Neutralizing anti-PA or anti-LF antibodies produced from lethal toxin challenge were quantified by a macrophage protection assay (see, e.g., Friedlander, *J. Biol. Chem.*, 261, 7123-7126 (1986)). A single intramuscular administration of a 2.5 µg dose of the rPA/Alhydrogel vaccine protected only 7.6% of the mice challenged with lethal toxin, while nearly all of the animals receiving a $3\times10^9$ pu dose of AdsechPA were protected. In addition, the same dose of AdsechPA was shown to offer partial protection to lethal toxin challenge as early as 11 days post administration, while the rPA/Alhydrogel vaccine offered no protection against lethal toxin challenge at the same time point.

The results of the example demonstrate the production of a rapid and efficient anti-PA immune response elicited by the inventive gene transfer vector, as well as protection against subsequent anthrax infection.

EXAMPLE 3

This example demonstrates a method of producing an anti-PA immune response using a human or chimpanzee adenoviral vector comprising a nucleic acid encoding a humanized immunogenic portion of PA and a heterologous sorting signal.

Using techniques known in the art and described herein, the sec-hPA-LAMP 1 expression construct of Example 1 is inserted into the E1 region of a replication-deficient chimpanzee adenoviral vector of strain C68 (AdC68sec-hPA-LAMP1). Mice from three different laboratory strains, C57B1/6, A/J, and ICR, are administered the Ad 5-based adenoviral vector of Example 1 (AdsechPA), or AdC68sec-hPA-LAMP 1 via any one of the following routes: intravenous injection, intramuscular injection, oral administration, nasal administration, and injection into the foot pad. As a control, the response produced by each adenoviral vector is compared to the response produced by recombinant PA in alum.

Immunized mice are assessed for anti-PA humoral responses by bleeding from the tail vein at multiple time points, including pre-vaccination, 1, 2, 4, 8, 16, and 26 weeks post infection (p.i.), and by quantifying anti-PA antibodies using ELISA. In addition to humoral responses, cell-mediated (i.e. T cell) responses are assessed at days 7 and 14 p.i. using the ELISPOT assay described above. At 4 and 16 weeks post infection, mice are challenged with PA+LF toxin or the Sterne strain of *B. anthracis*. Candidate gene transfer vectors that induce the strongest protective response are identified and reassessed at time points closer to the time of vector administration (i.e., days 1, 2, 3, 5, and 7 p.i.).

The efficacy of candidate adenoviral gene transfer vectors in the presence of preexisting anti-Ad5 neutralizing antibodies is assessed in mice pre-immunized with $1\times10^9$ pu of wild-type Ad5 four weeks prior to administration of candidate gene transfer vectors. The presence of anti-Ad5 neutralizing antibodies is determined as the inhibition of Ad5-induced cytopathic effect on A549 cells. Once optimal doses are determined as a result of the above described assays, the immune responses elicited by the "best" candidate Ad5 and/or AdC68 vaccines are assessed in naive and Ad5-immunized mice. The candidate vectors are administered in two doses administered four weeks apart, and in all possible combinations (i.e., Ad5 followed by Ad5, AdC68 followed by AdC68, Ad5 followed by AdC68, and AdC68 followed by Ad5).

This example demonstrates a method of producing an anti-PA immune response using a human or chimpanzee adenoviral vector comprising a nucleic acid encoding a humanized immunogenic portion of *Bacillus anthracis* protective antigen and a heterologous sorting signal.

EXAMPLE 4

This example demonstrates a method of producing an immune response against *Bacillus anthracis* in a host, which comprises administering to dendritic cells of the host a gene transfer vector comprising a nucleic acid sequence as described in Example 1.

Using methods described in, for example, U.S. Pat. Nos. 5,770,442 and 5,965,541, the penton base integrin-binding RGD domain and (separately) a seven-residue polylysine (pK7) sequence are engineered into the fiber knob domain of a replication-deficient Ad 5 adenoviral vector and an AdC68 adenoviral vector, each encoding a reporter gene (e.g., luciferase). Such modifications to the fiber protein of Ad 5, have been demonstrated to preferentially direct adenoviral infection to dendritic cells as described elsewhere herein.

Dendritic cell infection by the fiber-modified AdC68 vector is assessed by infecting human monocyte-derived DC with 100 plaque forming units (pfu)/cell of the fiber-modified AdC68 vector and incubating for 48 hours. Luciferase expression is measured using standard techniques and is indicative of DC gene transfer by the fiber-modfied AdC68 vector.

The fiber-modified Ad5 and AdC68 vectors most effective at DC gene transfer are engineered to contain the sec-hPA-LAMP1 expression construct (see Examples 1-3) and are tested using the mouse models described in Example 3. In this respect, both the humoral anti-PA immune response and the anti-lethal toxin protective immune response elicited by hPA expression are assessed and compared to the immune responses generated by identical Ad5 and AC68 gene transfer vectors with wild-type capsid proteins.

This example demonstrates a method of producing an immune response against *Bacillus anthracis* in a host by administering the inventive gene transfer vector to dendritic cells of the host All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A gene transfer vector comprising a nucleic acid sequence which encodes an exotoxin of *Bacillus anthracis* and a nucleic acid sequence which encodes a heterologous sorting signal, wherein the nucleic acid sequence encoding the exotoxin comprises SEQ ID NO: 1.

2. The gene transfer vector of claim 1, wherein the heterologous sorting signal directs the exotoxin to a subcellular sorting pathway.

3. The gene transfer vector of claim 2, wherein the subcellular sorting pathway is a lysosome pathway.

4. The gene transfer vector of claim 1, wherein the heterologous sorting signal is a lysosomal-associated membrane protein-1 sorting signal.

5. The gene transfer vector of claim 1, wherein the nucleic acid sequence further encodes a heterologous signal peptide.

6. The gene transfer vector of claim 5, wherein the heterologous signal peptide is a lysosomal-associated membrane protein-1 signal peptide.

7. The gene transfer vector of claim 1, which is a viral vector.

8. The gene transfer vector of claim 7, wherein the viral vector is an adenoviral vector.

9. The gene transfer vector of claim 8, wherein the adenoviral vector is replication-deficient.

10. The gene transfer vector of claim 9, wherein the adenoviral vector is a human adenoviral vector.

11. The gene transfer vector of claim 9, wherein the adenoviral vector is a non-human primate adenoviral vector.

12. The gene transfer vector of claim 11, wherein the adenoviral vector is a chimpanzee adenoviral vector.

13. A composition comprising the gene transfer vector of claim 1 and a pharmaceutically acceptable carrier.

* * * * *

SEQUENCE LISTING

<160> NUMBER OF SEQ ID NOS: 4

<210> SEQ ID NO 1
<211> LENGTH: 2295
<212> TYPE: DNA
<213> ORGANISM: Artificial
<220> FEATURE:
<223> OTHER INFORMATION: Synthetic B. anthracis gene for protective
      antigen with human-preferred codons
<220> FEATURE:
<221> NAME/KEY: CDS
<222> LOCATION: (1)..(2295)

<400> SEQUENCE: 1

```
atg aag aag cgc aag gtg ctg atc ccc ctg atg gcc ttg tcc acc atc      48
Met Lys Lys Arg Lys Val Leu Ile Pro Leu Met Ala Leu Ser Thr Ile
1               5                  10                  15 ctg gtg tcc agc acc ggc aac ctc gag gtg atc cag gcc gag gtg aag      96
Leu Val Ser Ser Thr Gly Asn Leu Glu Val Ile Gln Ala Glu Val Lys
                20                  25                  30 cag gag aac cgg ctg ctg aac gag tcc gag tcc agc tcc cag ggg ctg     144
Gln Glu Asn Arg Leu Leu Asn Glu Ser Glu Ser Ser Ser Gln Gly Leu
            35                  40                  45 ctg ggc tac tac ttc agc gac ttg aac ttc cag gcc cct atg gta gtg     192
Leu Gly Tyr Tyr Phe Ser Asp Leu Asn Phe Gln Ala Pro Met Val Val
        50                  55                  60 acc tcc tcc acc acc ggg gac ctg tcc atc ccc agc tcc gag ctg gag     240
Thr Ser Ser Thr Thr Gly Asp Leu Ser Ile Pro Ser Ser Glu Leu Glu
65                  70                  75                  80 aac atc ccc tcc gag aac cag tac ttc cag tcc gcc atc tgg tcc ggc     288
Asn Ile Pro Ser Glu Asn Gln Tyr Phe Gln Ser Ala Ile Trp Ser Gly
                85                  90                  95 ttc atc aag gtg aag aag agc gac gag tac acc ttc gcc acc tcc gcc     336
Phe Ile Lys Val Lys Lys Ser Asp Glu Tyr Thr Phe Ala Thr Ser Ala
                100                 105                 110 gac aac cac gtg acc atg tgg gtg gac gac cag gag gtg atc aac aag     384
Asp Asn His Val Thr Met Trp Val Asp Asp Gln Glu Val Ile Asn Lys
            115                 120                 125 gcc tcg aat tcc aac aag atc cgc ctg gag aag ggc cgc ctg tac cag     432
Ala Ser Asn Ser Asn Lys Ile Arg Leu Glu Lys Gly Arg Leu Tyr Gln
        130                 135                 140 atc aag atc cag tac cag cgc gag aac ccc acc gag aag ggc ttg gac     480
Ile Lys Ile Gln Tyr Gln Arg Glu Asn Pro Thr Glu Lys Gly Leu Asp
145                 150                 155                 160 ttc aag ttg tac tgg acc gac tcc cag aac aag aag gag gtg atc tcc     528
Phe Lys Leu Tyr Trp Thr Asp Ser Gln Asn Lys Lys Glu Val Ile Ser
                165                 170                 175 agc gac aac ctc cag ctg ccc gag ctg aag cag aag tcc tcc aac tcc     576
Ser Asp Asn Leu Gln Leu Pro Glu Leu Lys Gln Lys Ser Ser Asn Ser
                180                 185                 190 cgc aag aag cgc agc acc agc gcc ggc ccc acc gtg ccc gac cgc gac     624
Arg Lys Lys Arg Ser Thr Ser Ala Gly Pro Thr Val Pro Asp Arg Asp
            195                 200                 205 aac gac ggc atc ccc gac tcc ctg gag gtg gag ggc tac acc gtg gac     672
Asn Asp Gly Ile Pro Asp Ser Leu Glu Val Glu Gly Tyr Thr Val Asp
        210                 215                 220 gtc aag aac aag cgc acc ttc ctg tcc ccc tgg atc tcc aac atc cac     720
Val Lys Asn Lys Arg Thr Phe Leu Ser Pro Trp Ile Ser Asn Ile His
225                 230                 235                 240 gag aag aag ggc ctg acc aag tac aag tcc tcc ccc gag aag tgg agc     768
```

-continued

| | | |
|---|---|---|
| Glu Lys Lys Gly Leu Thr Lys Tyr Lys Ser Ser Pro Lys Trp Ser<br>245 250 255 | | |
| acc gcc tcc gac ccg tac agc gac ttc gag aag gtg acc ggc cgg atc<br>Thr Ala Ser Asp Pro Tyr Ser Asp Phe Glu Lys Val Thr Gly Arg Ile<br>260 265 270 | 816 | |
| gac aag aac gtg tcc ccc gag gcc cgc cac ccc ctg gtg gcc gcc tac<br>Asp Lys Asn Val Ser Pro Glu Ala Arg His Pro Leu Val Ala Ala Tyr<br>275 280 285 | 864 | |
| ccg ata gtg cac gtg gac atg gag aac atc atc ctc tcc aag aac gag<br>Pro Ile Val His Val Asp Met Glu Asn Ile Ile Leu Ser Lys Asn Glu<br>290 295 300 | 912 | |
| gac cag tcc acc cag aac acc gac agc cag acc cgc acc atc agc aag<br>Asp Gln Ser Thr Gln Asn Thr Asp Ser Gln Thr Arg Thr Ile Ser Lys<br>305 310 315 320 | 960 | |
| aac acc tcc acc agc agg acc cac acc agc gag gtg cac ggc aac gcc<br>Asn Thr Ser Thr Ser Arg Thr His Thr Ser Glu Val His Gly Asn Ala<br>325 330 335 | 1008 | |
| gag gtg cac gcg tcc ttc ttc gac atc ggc ggg agc gtg tcc gcc ggc<br>Glu Val His Ala Ser Phe Phe Asp Ile Gly Gly Ser Val Ser Ala Gly<br>340 345 350 | 1056 | |
| ttc agc aac tcc aac tcc agc acc gtc gcc atc gac cac tcc ctg tcc<br>Phe Ser Asn Ser Asn Ser Ser Thr Val Ala Ile Asp His Ser Leu Ser<br>355 360 365 | 1104 | |
| ctg gcc ggg gag cgc acc tgg gcc gag acc atg ggc ctg aac acc gcc<br>Leu Ala Gly Glu Arg Thr Trp Ala Glu Thr Met Gly Leu Asn Thr Ala<br>370 375 380 | 1152 | |
| gac acc gcc cgc ctg aac gcc aac atc cgc tac gtg aac acc ggg acc<br>Asp Thr Ala Arg Leu Asn Ala Asn Ile Arg Tyr Val Asn Thr Gly Thr<br>385 390 395 400 | 1200 | |
| gcc ccc atc tac aac gtg ctg ccc acc acc tcc ctg gtg ctg ggc aag<br>Ala Pro Ile Tyr Asn Val Leu Pro Thr Thr Ser Leu Val Leu Gly Lys<br>405 410 415 | 1248 | |
| aac cag acc ctc gcg acc atc aag gcc aag gag aac cag ctg agc cag<br>Asn Gln Thr Leu Ala Thr Ile Lys Ala Lys Glu Asn Gln Leu Ser Gln<br>420 425 430 | 1296 | |
| atc ctg gcc ccc aac aac tac tat ccc tcc aag aac ttg gcg ccc atc<br>Ile Leu Ala Pro Asn Asn Tyr Tyr Pro Ser Lys Asn Leu Ala Pro Ile<br>435 440 445 | 1344 | |
| gcc ctg aac gcc cag gac gac ttc agc tcc acc ccc atc acc atg aac<br>Ala Leu Asn Ala Gln Asp Asp Phe Ser Ser Thr Pro Ile Thr Met Asn<br>450 455 460 | 1392 | |
| tac aac cag ttc ctg gag ctg gag aag acc aag cag ctg cgc ctg gac<br>Tyr Asn Gln Phe Leu Glu Leu Glu Lys Thr Lys Gln Leu Arg Leu Asp<br>465 470 475 480 | 1440 | |
| acc gac cag gtg tac ggg aac atc gcc acc tac aac ttc gag aac ggc<br>Thr Asp Gln Val Tyr Gly Asn Ile Ala Thr Tyr Asn Phe Glu Asn Gly<br>485 490 495 | 1488 | |
| cgc gtg agg gtg gac acc gga tcc aac tgg agc gag gtg ctg ccg cag<br>Arg Val Arg Val Asp Thr Gly Ser Asn Trp Ser Glu Val Leu Pro Gln<br>500 505 510 | 1536 | |
| atc cag gag acc acc gcc cgc atc atc ttc aac ggc aag gac ctg aac<br>Ile Gln Glu Thr Thr Ala Arg Ile Ile Phe Asn Gly Lys Asp Leu Asn<br>515 520 525 | 1584 | |
| ctg gtg gag agg cgg atc gcg gcg gtg aac ccc agc gac ccc ctg gag<br>Leu Val Glu Arg Arg Ile Ala Ala Val Asn Pro Ser Asp Pro Leu Glu<br>530 535 540 | 1632 | |
| acc acc aag ccg gac atg acc ctg aag gag gcc ctg aag atc gcc ttc<br>Thr Thr Lys Pro Asp Met Thr Leu Lys Glu Ala Leu Lys Ile Ala Phe<br>545 550 555 560 | 1680 | |

```
ggc ttc aac gag ccg aac ggc aac ctc cag tac cag ggg aag gac atc   1728
Gly Phe Asn Glu Pro Asn Gly Asn Leu Gln Tyr Gln Gly Lys Asp Ile
            565                 570                 575 acc gag ttc gac ttc aac ttc gac cag caa acc tcc cag aac atc aag   1776
Thr Glu Phe Asp Phe Asn Phe Asp Gln Gln Thr Ser Gln Asn Ile Lys
        580                 585                 590 aac cag ctg gcg gag ctg aac gtg acc aac atc tac acc gtg ctg gac   1824
Asn Gln Leu Ala Glu Leu Asn Val Thr Asn Ile Tyr Thr Val Leu Asp
    595                 600                 605 aag atc aag ctg aac gcc aag atg aac atc ctg atc cgc gac aag cgc   1872
Lys Ile Lys Leu Asn Ala Lys Met Asn Ile Leu Ile Arg Asp Lys Arg
610                 615                 620 ttc cac tac gac cgc aac aac atc gcc gtg ggg gcc gac gag tcc gtg   1920
Phe His Tyr Asp Arg Asn Asn Ile Ala Val Gly Ala Asp Glu Ser Val
625                 630                 635                 640 gtg aag gag gcc cac cgc gag gtg atc aac tcc tcc acc gag ggc ctg   1968
Val Lys Glu Ala His Arg Glu Val Ile Asn Ser Ser Thr Glu Gly Leu
            645                 650                 655 ttg ctg aac atc gac aag gat atc cgc aag atc ctg tcc ggc tac atc   2016
Leu Leu Asn Ile Asp Lys Asp Ile Arg Lys Ile Leu Ser Gly Tyr Ile
        660                 665                 670 gtg gag atc gag gac acc gag ggg ctg aag gag gtg atc aac gac cgc   2064
Val Glu Ile Glu Asp Thr Glu Gly Leu Lys Glu Val Ile Asn Asp Arg
    675                 680                 685 tac gac atg ttg aac atc tcc agc ctg cgg cag gac ggc aag acc ttc   2112
Tyr Asp Met Leu Asn Ile Ser Ser Leu Arg Gln Asp Gly Lys Thr Phe
690                 695                 700 atc gac ttc aag aag tac aac gac aag ctg ccg ctg tac atc agc aac   2160
Ile Asp Phe Lys Lys Tyr Asn Asp Lys Leu Pro Leu Tyr Ile Ser Asn
705                 710                 715                 720 ccc aac tac aag gtg aac gtg tac gcc gtg acc aag gag aac acc atc   2208
Pro Asn Tyr Lys Val Asn Val Tyr Ala Val Thr Lys Glu Asn Thr Ile
            725                 730                 735 att aac ccc agc gag aac ggg gac acc agc acc aac ggg atc aag aag   2256
Ile Asn Pro Ser Glu Asn Gly Asp Thr Ser Thr Asn Gly Ile Lys Lys
        740                 745                 750 atc ctg atc ttt tcg aag aag ggc tac gag atc ggc taa               2295
Ile Leu Ile Phe Ser Lys Lys Gly Tyr Glu Ile Gly
    755                 760

<210> SEQ ID NO 2
<211> LENGTH: 764
<212> TYPE: PRT
<213> ORGANISM: Artificial
<220> FEATURE:
<223> OTHER INFORMATION: Synthetic B. anthracis gene for protective
      antigen with human-preferred codons

<400> SEQUENCE: 2

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
```

-continued

```
                85                  90                  95
Phe Ile Lys Val Lys Ser Asp Glu Tyr Thr Phe Ala Thr Ser Ala
            100                 105                 110
Asp Asn His Val Thr Met Trp Val Asp Asp Gln Glu Val Ile Asn Lys
            115                 120                 125
Ala Ser Asn Ser Asn Lys Ile Arg Leu Glu Lys Gly Arg Leu Tyr Gln
            130                 135                 140
Ile Lys Ile Gln Tyr Gln Arg Glu Asn Pro Thr Glu Lys Gly Leu Asp
145                 150                 155                 160
Phe Lys Leu Tyr Trp Thr Asp Ser Gln Asn Lys Lys Glu Val Ile Ser
                165                 170                 175
Ser Asp Asn Leu Gln Leu Pro Glu Leu Lys Gln Lys Ser Ser Asn Ser
                180                 185                 190
Arg Lys Lys Arg Ser Thr Ser Ala Gly Pro Thr Val Pro Asp Arg Asp
            195                 200                 205
Asn Asp Gly Ile Pro Asp Ser Leu Glu Val Glu Gly Tyr Thr Val Asp
            210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
                245                 250                 255
Thr Ala Ser Asp Pro Tyr Ser Asp Phe Glu Lys Val Thr Gly Arg Ile
                260                 265                 270
Asp Lys Asn Val Ser Pro Glu Ala Arg His Pro Leu Val Ala Ala Tyr
            275                 280                 285
Pro Ile Val His Val Asp Met Glu Asn Ile Ile Leu Ser Lys Asn Glu
            290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
            340                 345                 350
Phe Ser Asn Ser Asn Ser Ser Thr Val Ala Ile Asp His Ser Leu Ser
            355                 360                 365
Leu Ala Gly Glu Arg Thr Trp Ala Glu Thr Met Gly Leu Asn Thr Ala
            370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
                405                 410                 415
Asn Gln Thr Leu Ala Thr Ile Lys Ala Lys Glu Asn Gln Leu Ser Gln
                420                 425                 430
Ile Leu Ala Pro Asn Asn Tyr Tyr Pro Ser Lys Asn Leu Ala Pro Ile
            435                 440                 445
Ala Leu Asn Ala Gln Asp Asp Phe Ser Ser Thr Pro Ile Thr Met Asn
            450                 455                 460
Tyr Asn Gln Phe Leu Glu Leu Glu Lys Thr Lys Gln Leu Arg Leu Asp
465                 470                 475                 480
Thr Asp Gln Val Tyr Gly Asn Ile Ala Thr Tyr Asn Phe Glu Asn Gly
                485                 490                 495
Arg Val Arg Val Asp Thr Gly Ser Asn Trp Ser Glu Val Leu Pro Gln
            500                 505                 510
```

```
Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
        530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Val Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760
```

<210> SEQ ID NO 3
<211> LENGTH: 2430
<212> TYPE: DNA
<213> ORGANISM: Artificial
<220> FEATURE:
<223> OTHER INFORMATION: Synthetic B. anthracis gene for lethal factor
      with human-preferred codons

<400> SEQUENCE: 3

```
atgaacatca agaaggagtt catcaaggtg atcagcatgt cctgtctggt gaccgccatc      60
accctgagcg ccccgtctt catccccctg gtgcagggtg ccggcggcca tggtgacgtg     120
ggcatgcatg tgaaggagaa ggagaagaac aaggacgaga caagcgcaa ggacgaggag     180 cgcaacaaga cccaggagga gcacctgaag gagatcatga agcacatcgt gaagatcgag     240
gtgaaggggg aggaggccgt gaagaaggag gccgccgaga gctgctggga aggtgccc      300 tccgacgtgc tggagatgta caaggccatc ggcggcaaaa tctacatcgt ggacggcgac     360
atcaccaagc acatctccct ggaggccctg tccgaggaca gaagaagat caaggacatc     420 tacgggaagg acgccctgct gcacgagcac tacgtgtacg ccaaggaggg ctacgagccc     480
gtgctggtga tccagtcctc ggaggactac gtggagaaca ccgagaaggc cctgaacgtg     540
tactacgaga tcggcaagat cctgtccagg acatcctga gcaagatcaa ccagccctac     600
```

```
cagaagttcc tggacgtgct gaacaccatc aagaacgcct ccgactccga cggccaggac    660
ctgctgttca ccaaccagct gaaggagcac cccaccgact tctccgtgga attcctggag    720
cagaacagca cgaggtgcag gaggtgttcg cgaaggcctc gcctacta catcgagccc      780 cagcaccgcg acgtgctcca gctgtacgcc ccggaggcct caactacat ggacaagttc     840 aacgagcagg agatcaacct gtccctggag gagctgaagg accagcggat gctgtcccgc    900
tacgagaagt gggagaagat caagcagcac taccagcact ggagcgactc cctgtccgag    960
gagggccgcg gcctgctgaa gaagctccag atccccatcg agcccaagaa ggacgacatc   1020
atccactccc tgtcccagga ggagaaggag ctgctgaagc gcatccagat cgacagcagc   1080
gacttcctgt ccaccgagga gaaggagttc ctgaagaagc tccagatcga catccgcgac   1140
tccctgtccg aggaggagaa ggagctgctg aaccgcatcc aggtggacag cagcaacccc   1200
ctgtccgaga aggagaagga gttcctgaag aagctgaagc tggatatcca gcccacgac    1260 atcaaccaga ggctccagga caccggcggg ctgatcgaca gcccgtccat caacctggac   1320
gtgcgcaagc agtacaagag ggacatccag aacatcgacg ccctgctgca ccagtccatc   1380
ggcagcaccc tgtacaacaa aatctacctg tacgagaaca tgaacatcaa caacctgacc   1440
gccaccctgg cgcggaccct ggtggactcc accgacaaca ccaagatcaa ccgcggcatc   1500
ttcaacgagt tcaagaagaa cttcaagtac agcatctcca gcaactacat gatcgtggac   1560
atcaacgaga ggcccgccct ggacaacgag cgcctgaagt ggcgcatcca gctgtccccc   1620
gacacccgcg ccggctacct ggagaacggc aagctgatcc tccagcgcaa catcggcctg   1680
gagatcaagg acgtgcagat catcaagcag tccgagaagg agtacatcag gatcgacgcg   1740
aaggtggtgc ccaagagcaa gatcgacacc aagatccagg aggcccagct gaacatcaac   1800
caggagtgga acaaggccct ggggctgccc aagtacacca gcttatcac cttcaacgtg   1860 cacaaccgct acgcctccaa catcgtggag agcgcctacc tgatcctgaa cgagtggaag   1920
aacaacatcc agagcgacct gatcaagaag gtgaccaact acctggtgga cggcaacggc   1980
cgcttcgtgt tcaccgacat caccctcccc aacatcgccg agcagtacac ccaccaggac   2040
gagatttacg agcaggtgca ctccaagggg ctgtacgtgc ccgagtcccg ctccatcctg   2100
ctccacggcc cctccaaggg cgtggagctg aggaacgaca gcgagggctt catccacgag   2160
ttcggccacg ccgtggacga ctacgccggc tacctgctgg acaagaacca gtccgacctg   2220
gtgaccaact ccaagaagtt catcgacatc ttcaaggagg aggggagcaa cctgacctcg   2280
tacgggcgca ccaacgaggc ggagttcttc gccgaggcct tcaggctgat gcactccacg   2340
gaccacgccg agcgcctgaa ggtgcagaag aacgccccga agaccttcca gttcatcaac   2400
gaccagatca agttcatcat taattcctag                                    2430
```

<210> SEQ ID NO 4
<211> LENGTH: 2403
<212> TYPE: DNA
<213> ORGANISM: Artificial
<220> FEATURE:
<223> OTHER INFORMATION: Synthetic B. anthracis gene for edema factor
      with human-preferred codons

<400> SEQUENCE: 4

```
atgacccgca acaagttcat ccccaacaag ttcagcatca tctccttctc cgtgctgctg     60
ttcgccatct cctcctccca ggcgatcgag gttaacgcca tgaacgagca ctacaccgag    120
agcgacatca agcgcaacca caagaccgag aagaacaaga ccgagaagga gaagttcaag    180
```

-continued

```
gacagcatca acaacctggt gaagaccgag ttcaccaacg agaccctgga caagatccag      240
cagacccagg acctgctgaa gaagatcccc aaggacgtgc tggaaatcta cagcgagctg      300
ggcggcgaga tttacttcac cgacatcgac ctggtggagc acaaggagct gcaggacctg      360
agcgaggagg agaagaacag catgaacagc cgcggcgaga aggtgccgtt cgcctcccgc      420
ttcgtgttcg agaagaagag ggagaccccc aagctgatca tcaacatcaa ggactacgcc      480
atcaacagcg agcagagcaa ggaggtgtac tacgagatcg gcaaggggat ctccctggac      540
atcatcagca aggacaagtc cctgacccc gaattcctga acctgatcaa gagcctgagc      600
gacgacagcg acagcagcga cctgctgttc agccagaagt caaggagaa gctggagctg      660 aacaacaaga gcatcgacat caacttcatc aaggagaacc tgaccgagtt ccagcacgcg      720
ttctccctgg cgttctccta ctacttcgcc cccgaccacc gcacggtgct ggagctgtac      780 gccccgaca tgttcgagta catgaacaag ctggagaagg ggggcttcga aagatcagc      840 gagagcctga agaaggaggg cgtggagaag acaggatcg acgtgctgaa gggcgagaag      900
gccctgaagg cctccggcct ggtgcccgag cacgccgacg ccttcaagaa gatcgcccgc      960
gagctgaaca cctacatcct gttcaggccc gtgaacaagc tggccaccaa cctgatcaag     1020
agcggcgtgg ccaccaaggg cctgaacgtg cacggcaaga gctcggactg ggggcccgtg     1080
gccggctaca tccccttcga ccaggacctg tccaagaagc acggcagca gctggccgtc     1140 gagaagggca acctggagaa caagaagtcc atcaccgagc acgagggcga gatcggcaag     1200 atcccctga agctggacca cctgcgcatc gaggagctga aggagaacgg gatcatcctg     1260
aagggcaaga aggagatcga caacggcaag aagtactacc tgctggagtc gaacaaccag     1320
gtgtacgagt ccgcatcag cgacgagaac aacgaggtgc agtacaagac caaggagggc     1380
aagatcaccg tgctggggga aagttcaac tggcgcaaca tcgaggtgat ggccaagaac     1440 gtggagggg tcctgaagcc gctgaccgcc gactacgacc tgttcgccct ggcccccagc     1500
ctgaccgaga tcaagaagca gatccccag aaggagtggg acaaggtggt gaacaccccc     1560
aactccctgg agaagcagaa gggcgtgacc aacctgctga tcaagtacgg catcgagagg     1620
aagccggact ccaccaaggg cacctgtcc aactggcaga agcagatgct ggaccgcctg     1680 aacgaggcc tcaagtacac cggctacacc gggggggacg tggtgaacca tggcaccgag     1740
caggacaacg aggagttccc cgagaaggac aacgaaatct tcatcatcaa ccccgagggc     1800
gagttcatcc tgaccaagaa ctgggagatg accggccgct tcatcgagaa gaacatcacg     1860
ggcaaggact acctgtacta cttcaaccgc tcctacaaca agatcgcccc cggcaacaag     1920
gcctacatcg agtggaccga cccgatcacc aaggccaaga tcaacaccat ccccacgtcc     1980
gccgagttca tcaagaacct gtccagcatc cgccgctcct ccaacgtggg cgtgtacaag     2040
gacagcggcg acaaggacga gttcgccaag aaggagagcg tgaagaagat cgccggctac     2100
ctgtccgact actacaactc cgccaaccac atcttctccc aggagaagaa gcgcaagatt     2160
tccatcttcc gcggcatcca ggcctacaac gagatcgaga cgtgctgaa gtccaagcag     2220 atcgccccg agtacaagaa ctacttccag tacctgaagg agaggatcac caaccaggtg     2280
cagctgctgc tgacccacca gaagtccaac atcgagttca gctgctgta caagcagctg     2340 aacttcaccg agaacgagac ggacaacttc gaggtcttcc agaagatcat cgatgagaag     2400
tga                                                                   2403
```